(12) United States Patent
Parker

(10) Patent No.: US 7,931,910 B2
(45) Date of Patent: Apr. 26, 2011

(54) PESTICIDAL COMPOSITIONS AND METHODS

(75) Inventor: Diana L. Parker, Brentwood Bay (CA)

(73) Assignee: W. Neudorff GmbH KG, Emmerthal (DE)

(*) Notice: Subject to any disclaimer, the term of this patent is extended or adjusted under 35 U.S.C. 154(b) by 1103 days.

(21) Appl. No.: 11/623,889

(22) Filed: Jan. 17, 2007

(65) Prior Publication Data

US 2007/0134284 A1  Jun. 14, 2007

Related U.S. Application Data

(62) Division of application No. 10/657,419, filed on Sep. 8, 2003, now Pat. No. 7,537,778.

(60) Provisional application No. 60/413,688, filed on Sep. 26, 2002.

(51) Int. Cl.
*A01N 25/32* (2006.01)
*A01N 59/26* (2006.01)
*A01N 57/20* (2006.01)
*A01N 57/12* (2006.01)

(52) U.S. Cl. .......... 424/406; 424/84; 424/405; 424/407; 424/409; 424/410; 424/417; 424/418; 424/419; 424/420; 424/421; 424/601; 424/602; 424/603; 424/604; 424/605; 424/625; 424/630; 424/641; 424/647; 424/648; 424/724; 514/102; 514/131; 514/140; 514/141; 514/142

(58) Field of Classification Search .................. None
See application file for complete search history.

(56) References Cited

U.S. PATENT DOCUMENTS

| 3,786,079 | A | 1/1974 | Yonezawa |
| 5,206,228 | A | 4/1993 | Collins |
| 5,437,870 | A | 8/1995 | Puritch et al. |
| 5,854,309 | A | 12/1998 | Blount |
| 6,117,823 | A | 9/2000 | Smiley |
| 6,239,166 | B1 | 5/2001 | Black |
| 6,258,750 | B1 | 7/2001 | Simpson et al. |
| 6,323,153 | B1 | 11/2001 | Smiley |
| 6,352,706 | B1 | 3/2002 | Puritch |
| 6,972,273 | B2 | 12/2005 | Sedun et al. |

FOREIGN PATENT DOCUMENTS

| AU | 199877420 | 10/1998 |
| AU | 199941078 | 2/2000 |
| EP | 0 836 917 | 4/1998 |
| GB | 2184439 A | 6/1987 |
| GB | 2 368 284 | 5/2002 |
| WO | WO 99 39576 | 8/1999 |
| WO | WO 01/91555 | * 12/2001 |
| WO | WO 02/078448 | * 10/2002 |

OTHER PUBLICATIONS

Terranova et al., Effect of a Chelating Agent (EDTA) on the Tobacco Hornworm, Journal of Economic Entomology (1970), 63(3), 886-91.
Sell et al., "Chelating Agents Suppress Pupation of the Cabbage Looper", Journal of Economic Entomology (1968), vol. 61, pp. 946-949.

* cited by examiner

*Primary Examiner* — Neil Levy
(74) *Attorney, Agent, or Firm* — Nutter McClennen & FIsh LLP

(57) ABSTRACT

The present invention provides an environmentally compatible, pesticidal composition and method for the control of insect pests. The composition includes two components. The first component is a chelating agent, a metal complex of a chelating agent, and mixtures thereof, and the second component is preferably a carrier material.

24 Claims, No Drawings

PESTICIDAL COMPOSITIONS AND METHODS

CROSS-REFERENCE TO RELATED APPLICATIONS

This application is a divisional of U.S. application Ser. No. 10/657,419, filed on Sep. 8, 2003, entitled "Pesticidal Compositions and Methods," and further claims priority from U.S. Provisional Patent Application Ser. No. 60/413,688, filed on Sep. 26, 2002, entitled "Ingestible Pesticidal Composition," the disclosures of which are expressly incorporated by reference herein.

FIELD OF THE INVENTION

The present invention relates to environmentally safe pesticides, and more particularly to a pesticidal formulation containing chelating agents and/or their metal complexes that are effective to control insect pests.

BACKGROUND OF THE INVENTION

In recent years, concerns have been raised about the potential danger of synthetic pesticides to humans and other non-target organisms. With this increased concern about toxicity and environmental safety, there has been a renewed interest in the use of safer substances, including natural active ingredients, for pest control. Chelating agents have a long history of human use and are widely used in the food, cosmetic and pharmaceutical industries. One of the best known pharmaceutical uses of chelating agents is in the treatment of heavy metal poisoning (Remington's Pharmaceutical Sciences). Chelating agents are also used extensively as stabilizers because they prevent oxidation of susceptible compounds by sequestering metal ions, which can catalyze degradation reactions.

Metal chelates are reported in the literature as control agents for molluscs (slugs and snails). For example, U.S. Pat. No. 5,437,870 (Puritch et al.) discloses an ingestible molluscicide having a carrier (e.g., a bait), a simple iron compound, and ethylene diamine tetracetic acid (EDTA), salts of EDTA, hydroxyethlene triamine diacetic acid, (HEDTA) or salts of HEDTA. U.S. Pat. No. 6,352,706 of Puritch also discloses an ingestible molluscicide containing a simple metal compound, an activity enhancing additive such as ethylene diamine disuccinic acid (EDDS) and derivatives thereof, and a carrier material edible to molluscs. Australian Patent Application No. 77420/98 of Young also discloses a stomach-action molluscicide that includes a metal complexone (i.e., iron EDTA) and a carrier.

The herbicidal (weed), algaecidal (algae) and fungicidal (plant disease) activity of metal chelates is also reported. For example, U.S. Pat. No. 6,323,153 of Smiley teaches using various chelated calcium and magnesium salts to control the growth of various weeds in lawns. Smiley also discloses, in U.S. Pat. No. 6,117,823, the use of aliphatic carboxylic acid diesters, such as dimethyl succinate and dimethyl glutarate, as non-selective herbicides. Further examples include U.S. Pat. No. 6,258,750 of Simpson, which teaches an algaecidal, herbicidal and/or fungicidal composition including a metal, the chelating agent ethylene diamine disuccinic acid (EDDS) or a salt thereof, and a source of calcium and chloride ions.

While the use of metal chelates and chelating agents in molluscicides, herbicides, algaecides, and fungicides is known, there is still a need for an environmentally safe pesticidal formulation for controlling insect pests.

SUMMARY OF THE INVENTION

The present invention is directed to an environmentally safe pesticide for the control of insect pests. The pesticidal composition preferably includes two main components. The first component, which is preferably the active ingredient, is a chelating agent, a metal complex of a chelating agent, or mixtures thereof, and the second component is a carrier material. The carrier material can be a liquid or a solid carrier, but it is preferably effective to promote ingestion and to attract specific targeted pests. The disclosed pesticidal compositions can be used in dry or liquid form as baits. The composition can also be applied to substrates or plants frequented by pests.

The present invention also provides a method for killing insect pests using a pesticidal composition having a first component, such as a chelating agent, a metal complex of a chelating agent, or mixtures thereof, and a carrier material. The method includes the step of applying the pesticidal composition to an area infested with insect pests, such that the insect pests can ingest the pesticidal composition. The first component is preferably present at an amount that is effective to kill the insect pests upon ingestion.

DETAILED DESCRIPTION OF THE INVENTION

The present invention provides an environmentally compatible, pesticidal composition and method for the control of insect pests. In general, the composition includes two main components. The first component is preferably a chelating agent, a metal complex of a chelating agent, or mixtures thereof, and the second component is a carrier material. The composition is preferably used as an ingestible poison effective to kill insect pests.

Although the mode of action of chelators as insecticides is not known at this time, it is possible that chelators disrupt critical processes in insect pests by removing metal ion catalysts needed for enzyme systems. As well as cofactors for some enzyme systems, metals themselves play important roles in the digestive tracts of insect pests. Removal of metals by chelators could have serious consequences on insect pest metabolism and physiology. As shown herein, chelating agents and their metal complexes represent novel, effective control agents for insect pests. Chelating agents and their metal complexes have proven to be non-toxic to humans and household animals, and have been used extensively in the food, cosmetic and pharmaceutical industries. Although chelating agents and their metal complexes are documented in the literature as effective control agents against molluscs and weeds, the use of ingestible chelating agents to combat insect pests has not heretofore been known. Unlike the rapid degradation observed with many natural insecticides derived from plants, good stability is anticipated with dry formulations containing chelating agents, metal complexes of a chelating agent, or mixtures thereof.

The first component of the pesticidal composition is the active ingredient which includes a chelating agent or its metal complex. A chelating agent is a substance whose molecules can form several bonds to a single metal ion, and thus, as a result, the chelating agent and a metal ion will form a metal chelate. The chelating agent can be added in a variety of forms. By way of non-limiting example, one or more chelating agents can be added as a salt. Preferably, in this embodiment, the chelating agent is added as a sodium salt, a potassium salt, a calcium salt, a zinc salt, an ammonium salt, an amine salt, an amide salt, and combinations thereof.

Suitable chelating agents include, for example, aconitic acid, alanine diacetic acid (ADA), alkoyl ethylene diamine triacetic acids (e.g., lauroyl ethylene diamine triacetic acids (LED3A)), aminotri(methylenephosphonic acid) (ATMP), asparticaciddiacetic acid (ASDA), asparticacidmonoacetic acid, diamino cyclohexane tetraacetic acid (CDTA), citraconic acid, citric acid, 1,2-diaminopropanetetraacetic acid (DPTA-OH), 1,3-diamino-2-propanoltetraacetic acid (DTPA), diethanolamine, diethanol glycine (DEG), diethylenetriaminepentaacetic acid (DTPA), diglycolic acid, dipicolinic acid (DPA), ethanolaminediacetic acid, ethanoldiglycine (EDG), ethionine, ethylenediamine (EDA), ethylenediaminediglutaric acid (EDDG), ethylenediaminedi(hydroxyphenylacetic acid (EDDHA), ethylenediaminedipropionic acid (EDDP), ethylenediaminedisuccinate (EDDS), ethylenediaminemonosuccinic acid (EDMS), ethylenediaminetetraacetic acid (EDTA), ethyleneglycolaminoethylestertetraacetic acid (EGTA), gallic acid, glucoheptonic acid, glutamicaciddiacetic acid (GLDA), glutaric acid, gluconic acid, glyceryliminodiacetic acid, glycinamidedisuccinic acid (GADS), glycoletherdiaminetetraacetic acid (GEDTA), 2-hydroxyethyldiacetic acid, hydroxyethylenediaminetriacetic acid (HEDTA), hydroxyethyldiphosphonic acid (HEDP), hydroxyiminodiacetic acid (HIDA), iminodiacetic acid (IDA), iminodisuccinic acid (IDS), itaconic acid, lauroyl ethylene diamine triacetic acids (LED3A), methylglycinediacetate (MGDA), methyliminodiacetic acid (MIDA), monoethanolamine, nitrilotriacetic acid (NTA), nitrilotripropionic acid (NPA), saccharates, salicylic acid, serinediacetic acid (SDA), sorbic acid, succinic acid, tartaric acid, tartronic acid, triethanolamine, triethylenetetraamine, and combinations thereof. Preferably, the chelating agent is an aminopolycarboxylic acid, an amine, an amide, a carboxylic acid, a phosphonic acid and combinations thereof. More preferably, the chelating agent is EDTA, HEDTA, EDDS, HEDP, DTPA and combinations thereof. Other suitable chelating agents capable of complexing metal ions include, for example, amino acids, such as aspartic acid, glutamic acid, and lysine, as well as proteins, such as whey powder, casein, and albumen.

As stated above, the first component can include the complex of a chelating agent. Suitable metal complexes include, but are not limited to, those containing Group I and II metals, and transition metals. More preferably, the metal complexes include aluminum ions, copper ions, iron ions, manganese ions, nickel ions, zinc ions, and combinations thereof. These metal ions can be added in a variety of ionic states. The metal ions can be added in a variety of forms. For example, metal ions can be added to the composition as a metal salt which reacts with the chelating agent to form a metal chelate. Preferably, when the metal ions are added as a salt, they are added as, for example, a chloride salt, a sulfate salt, a nitrate salt, a citrate salt, a phosphate salt, a carbonate salt, an acetate salt, a hydroxide salt, a chelate salt, a sulfide salt, a sulfite salt, a succinate salt, a gluconate salt, a lactate salt, a formate salt, a nitrite salt, a salicylate salt, a carboxylic acid salt, and in combinations of these salts.

The composition of the invention typically includes a second component which is a carrier material. A variety of materials can be used to form the carrier material, including both liquid and solid carrier materials. In one embodiment, the carrier can be a food source that is effective to promote ingestion and/or attract specific target pests. Examples of suitable food sources for use in bait formulations include, but are not limited to, wheat flour, wheat cereal, bran, molasses, vinegar, agar, gelatin, pet food, wheat, soy products, oats, corn, corn cob, vegetable oils, citrus mash, rice, fruits, fish by-products, sugars, coated vegetable seeds, coated cereal seeds, dairy products, whey powder, casein, albumen, blood meal, bone meal, yeast, fats, beer products, paper fiber, cellulose, gelatin and mixtures thereof.

In an alternative embodiment, the carrier can be a liquid carrier that is effective as a bait or that can leave a residue on the insect pest, which can lead to ingestion and subsequently death. For liquid formulations, water, alcohols, vinegar, plant-derived oils, mineral oils, glycerol, glycols, or combinations thereof can serve as the carrier. The formulation can also include a food source, such as sugar, that can be mixed with the liquid carrier.

To enhance ingestion and attraction of pests, other suitable additives can include but are not limited to attractants, phagostimulants, or combinations thereof. These additives can be incorporated within the composition in a dry or liquid form. Non-food carriers can also be used alone or combined with food materials or attractants that promote ingestion. Examples of non-food carriers suitable as additives include cellulose complexes, such as Biodac® (available from Kadant GranTek Inc., Granger, Ind.), sand, clay, silica, polyacrylic acid polymers, polyacrylimide acid polymers, diatomaceous earth, alginate, and wax.

In addition to the first and second components, the pesticidal composition can optionally include other components, such as other formulation enhancing additives. By way of non-limiting example, the composition can include preservatives, taste-altering additives, water-proofing agents, antioxidants, suspending agents, UV stabilizers, odor masking agents, and anti-microbial agents.

Suitable preservatives include Legend MK®, available from Rohm & Hass Company of Philadelphia, Pa. and CA-24, available from Dr. Lehmann and Co. of Memmingen/Allgäiu, Germany. Preservatives such as these can normally be mixed with water to form a stock solution to be added to the formulation at a concentration in the range of about 10-750 ppm.

Waterproofing agents, which can also act as binders, can be added to the composition to improve the weatherability of the composition. These are typically water insoluble compounds such as waxy materials and other hydrocarbons. Examples of suitable waterproofing agents include paraffin wax, stearate salts, beeswax, and similar compounds.

Antioxidants can be useful additives for the composition in order to reduce the effect of oxidation. Examples of suitable antioxidants include butylated hydroxytoluene (BHT), butylated hydroxy anisole (BHA) and natural antioxidants such as Vitamin E and ascorbic acid. UV protectants include UV absorbers such as PABA and benzophenones, and dyes and fillers with UV absorbing properties.

Suspending agents may be added to improve the stability and shelf life of the composition. Examples of suitable suspending agents include gum arabic, guar gum, sodium caseinate, polyvinyl alcohol, magnesium aluminum silicate (Van Gel B) from R.T. Vanderbilt Co. Inc., Norwalk, Conn., locust bean gum, xanthan gum, kelgum and mixtures thereof. Other suitable thickeners include polyacrylic acid polymers such as Pemulen and Carbopol from BF Goodrich Corp., Brecksville, Ohio.

It may also be desirable to include within the composition taste altering compounds that render the composition unpalatable to animals, such as humans and pets. Exemplary compositions include those having a bitter taste. One such compound available commercially is BITREX® from McFarlane Smith Ltd. of Edinburgh, Scotland. These compounds are typically added at a very low concentration. For example, a 0.1% BITREX solution can be added to the composition at about 1% to 2% by weight of the total composition.

In use, the formulation of the pesticidal composition of the present invention can vary. Preferably, the composition is prepared as a ready-to-use solution, a liquid concentrate, or a dry concentrate. The compositions can also be in the form of a liquid, solid, or semi-solid bait, or as a pre-treated strip or backing material covered with the composition in the dry form. For ingestion, chelators can be typically formulated as attractive baits. Alternatively, or in addition, formulations can be applied to the target insects whereby toxic quantities will be consumed from insect body surfaces via preening and grooming behaviors.

To prepare a composition according to one embodiment of the present invention, a suitable amount of the first component, e.g., a metal chelate, a chelating agent, a salt of a chelating agent, and mixtures thereof, is blended in dry form with a carrier material. Thereafter, other ingredients, such as phagostimulants and waterproofing agents, can be blended and mixed with the pesticidal composition.

In another embodiment, the composition can be prepared as a liquid formulation. The chelating agent is added first to an aqueous carrier, either as a salt or by combining the acid form of the chelating agent with an appropriate base. A metal is then added in the form of a soluble salt and allowed to react with the chelating agent. Thereafter, other ingredients, such as phagostimulants and waterproofing agents, can be blended and mixed with the pesticidal composition.

The concentration of the chelating agent in the pesticidal compositions of the present invention can vary. Preferably, the chelating agent is present at a concentration in the range of about 0.25% to about 40%, and more preferably is present at a concentration in the range of about 0.5% to 30%. When formulated and presented in liquid form, chelating agent concentrations typically range from 0.5% to 10%. Alternatively, liquid formulations can be applied to surfaces and allowed to dry. Evaporation of water during the drying process significantly increases the concentration of chelating agent relative to other bait components, with typical concentrations of chelating agents increasing to as high as 40%.

The pH of the pesticidal solution can also vary, but preferably, the pesticidal compositions of the present invention are effective over a wide range of pH values. If necessary, the composition can include pH-adjusting additives. Suitable pH-adjusting additives include, for example, calcium carbonate, potassium carbonate, hydrochloric acid, potassium hydroxide, ascorbic acid, tartaric acid, citric acid, and combinations thereof. Such additives are preferably used at a concentration in the range of about 0.05 to 5.0% by weight.

Since the composition is substantially nontoxic to humans or animals, the composition can be applied in domestic areas, including in and around dwellings.

The pesticidal composition is effective against a wide range of insect pests including, but not limited to, aphids, leafhoppers, whitefly, sawfly larvae, caterpillars, beetles, cockroaches, earwigs, ants, flies, mosquitoes, wasps, and silverfish.

The following non-limiting examples serve to further illustrate the present invention.

EXAMPLE 1

Formulations containing sucrose and sodium EDTA were applied to glass microscope slides using an Eppendorf pipette (200 μL/rep). For fresh treatments, slides were allowed to dry overnight. For storage treatments, slides were prepared 20 days previously and left uncovered in the laboratory prior to use. Adult house flies (4 day old) were anesthetized with $CO_2$ and transferred to 250 ml clear plastic cups containing a treated microscope slide, a small amount of granulated sugar and a water reservoir. Cups were covered with fine netting secured with rubber bands. Treatments consisted of 8 replicates of 5 insect pests each. Mortality was assessed 3 and 6 days after fly introduction.

TABLE 1

|   | Treatment | Storage Conditions | Mean % Mortality 3 Day | Mean % Mortality 6 Day |
|---|---|---|---|---|
| 1. | 10% sodium EDTA (pH 8) + 25% sucrose | 20 Days | 47.5 | 92.5 |
| 2. | 10% sodium EDTA (pH 10) + 25% sucrose | 20 Days | 40.0 | 80.0 |
| 3. | 1% sodium EDTA (pH 10) + 25% sucrose | 20 Days | 20.0 | 35.0 |
| 4. | 25% sucrose | 20 Days | 2.5 | 2.5 |
| 5. | 10% sodium EDTA (pH 8) + 25% sucrose | Fresh | 74.4 | 97.4 |
| 6. | 10% sodium EDTA (pH 10) + 25% sucrose | Fresh | 32.5 | 82.5 |
| 7. | 1% sodium EDTA (pH 10) + 25% sucrose | Fresh | 40.0 | 72.5 |
| 8. | 25% sucrose | Fresh | 0.0 | 2.5 |
| 9. | Untreated | Fresh | 0.0 | 0.0 |

Table 1 illustrates the mortality of adult house flies exposed to treatments and assessed after 3 and 6 days. High mortality of adult house flies was observed with 10% sodium EDTA baits prepared fresh or after 20 days storage (Table 1). Some activity was also observed with 1% sodium EDTA formulations. Baits containing 10% sodium EDTA baits were effective at both pH 8 and pH 10.

EXAMPLE 2

Formulations containing sucrose and sodium EDTA were applied to glass microscope slides using an Eppendorf pipette (200 μL/rep). Adult house flies (4 day old) were anesthetized with $CO_2$ and transferred (50 flies per replicate) to cages (60×60×60 cm). Cages contained two treated slides on the cage floor, a petri dish with a water reservoir and a sugar cube. Treatments consisted of 1 replicate of 50 flies each. Mortality was assessed 4 and 6 days after fly introduction.

TABLE 2

| Treatment | Mean % Mortality 4 Day | Mean % Mortality 6 Day |
|---|---|---|
| 1. 10% sodium EDTA + 25% sucrose | 42.0 | 100.0 |
| 2. Azamethiphos fly strips | 36.0 | 66.8 |
| 3. Untreated | 2.0 | 2.0 |

Table 2 illustrates the mortality of adult house flies exposed to treatments in cages and assessed after 4 and 6 days. After 6 days, high mortalities were observed with 10% sodium EDTA baits in a cage bioassay (Table 2). Sodium EDTA baits resulted in higher adult house fly mortalities than commercially sold azamethiphos fly strips.

EXAMPLE 3

Formulations containing sucrose and sodium EDTA were applied to glass microscope slides using an Eppendorf pipette (200 μL/rep). Adult house flies (5 day old) were anesthetized with $CO_2$ and transferred (50 flies per replicate) to cages (60×60×60 cm). Cages contained two treated slides on the cage floor, a petri dish with a water reservoir and a sugar cube. Treatments consisted of 2 replicates (cages). Mortality was assessed 2, 3 and 7 days after fly introduction.

TABLE 3

| Treatment | Mean % Mortality 2 Day | Mean % Mortality 3 Day | Mean % Mortality 7 Day |
|---|---|---|---|
| 1. 10% sodium EDTA + 25% sucrose | 35.0 | 69.0 | 100.0 |
| 2. Azamethiphos fly strips | 25.0 | 44.0 | 78.6 |
| 3. 25% sucrose | 2.0 | 3.0 | 2.0 |

Table 3 illustrates the mortality of adult house flies exposed to treatments in cages and assessed after 2, 3 and 7 days. After 7 days, complete (100%) mortality of adult house flies was observed with a 10% sodium EDTA bait (Table 3). The chelator bait resulted in higher adult house fly mortalities than a commercially sold azamethiphos fly strip.

EXAMPLE 4

Formulations were applied to the center of glass microscope slides using an Eppendorf pipette (200 µL/rep) and left uncovered in the laboratory for two weeks prior to testing. Small American cockroach nymphs from a laboratory colony were anesthetized with $CO_2$ and transferred to inverted petri dishes containing a filter paper, a small amount of granulated sugar and a water wick. Treatments consisted of 2 replicates of 3 insect pests each. Mortality was assessed 6 and 12 days following treatment.

TABLE 4

| Treatment | Mean % Mortality 6 Day | Mean % Mortality 12 Day |
|---|---|---|
| 1. 10% sodium EDTA + 25% sucrose | 50.0 | 83.3 |
| 2. Untreated | 16.7 | 16.7 |

Table 4 illustrates the mortality of small American cockroach nymphs exposed to treatments and assessed after 6 and 12 days. Sodium EDTA formulated with sucrose in a dried down layer resulted in moderate mortality of small American cockroach nymphs after 6 days and good mortality after 12 days (Table 4).

EXAMPLE 5

Braided cotton rolls were saturated with treatments. Vinegar gnats from a laboratory colony were anesthetized with $CO_2$ and transferred to inverted petri dishes containing a filter paper, a small amount of granulated sugar and a water wick. Each dish also contained a treated cotton roll. Treatments consisted of 8 replicates of 5 insect pests each. Mortality was 5 days after fly introduction.

TABLE 5

| Treatment | Mean % Mortality |
|---|---|
| 1. 10% sodium EDTA (pH 10) + 25% sucrose | 7.5 |
| 2. 10% sodium EDTA (pH 8) + 25% sucrose | 12.5 |
| 3. 1% sodium EDTA (pH 10) + 25% sucrose | 12.5 |
| 4. 10% sodium EDTA (pH 10) + 25% sucrose + 2.5% Brewer's Yeast | 52.5 |

TABLE 5-continued

| Treatment | Mean % Mortality |
|---|---|
| 5. 10% sodium EDTA (pH 8) + 25% sucrose + 2.5% Brewer's Yeast | 65.0 |
| 6. 1% sodium EDTA (pH 10) + 25% sucrose + 2.5% Brewer's Yeast | 57.5 |
| 7. 10% sodium EDTA (pH 10) + 25% sucrose + 10% Brewer's Yeast | 62.5 |
| 8. 10% sodium EDTA (pH 8) + 25% sucrose + 10% Brewer's Yeast | 57.5 |
| 9. 1% sodium EDTA (pH 10) + 25% sucrose + 10% Brewer's Yeast | 7.5 |
| 10. 25% sucrose | 5.0 |
| 11. Untreated | 8.1 |

Table 5 illustrates the mortality of adult vinegar gnats (Drosophila sp.) exposed to treatments and assessed after 5 days. Some activity against adult vinegar gnats (Drosophila sp.) was observed with sodium EDTA formulations presented as liquids in saturated wicks (Table 5). The addition of brewer's yeast to sodium EDTA baits, significantly increased adult vinegar gnat mortality.

EXAMPLE 6

Formulations were applied to the center of glass microscope slides using an Eppendorf pipette (200 µL/rep) and they were allowed to dry overnight. Adult house flies (4 day old) were anesthetized with $CO_2$ and then transferred to 4.2L Rubbermaid tubs with mesh lids containing a treated microscope slide, a petri dish containing a sugar cube, and a water reservoir. Treatments consisted of 4 replicates of 20 insect pests each. Mortality was assessed 5 days after fly introduction.

| Treatment | Mean % Mortality |
|---|---|
| 1. 7.5% Na$_4$EDTA (no food additives) | 1.3 |
| 2. 7.5% Na$_4$EDTA + 25% sucrose | 63.8 |
| 3. Sucrose | 0.0 |

Table 6 illustrates the mortality of adult house flies exposed to treatments and assessed after 5 days. Moderate mortality of adult house flies was observed with sodium EDTA in a dried layer with 25% sucrose (Table 6). Poor activity was observed with sodium EDTA without food additives.

EXAMPLE 7

Formulations were applied to the center of glass microscope slides using an Eppendorf pipette (200 µL/rep), and they were allowed to dry overnight. Adult house flies (3-5 day old) were anesthetized with $CO_2$ and transferred to 4.2L Rubbermaid tubs with mesh lids containing one treated microscope slide and a petri dish containing a sugar cube, and a water reservoir. Treatments consisted of 4 replicates of 20 insect pests each. Mortality was assessed 4, 6 and 14 days after fly introduction.

TABLE 7

| Treatment | Mean % Mortality 4 days | Mean % Mortality 6 days |
|---|---|---|
| 1. 7.5% Na$_4$EDTA (no food additives) | 2.5 | 3.8 |
| 2. 7.5% Na$_4$EDTA + Silwet L77 (no food additives) | 0.0 | 1.3 |
| 3. 7.5% Na$_4$EDTA + 25% sucrose + Silwet L77 | 23.8 | 67.5 |
| 4. 7.5% Na$_4$EDTA + 25% sucrose | 42.5 | 82.5 |
| 5. 25% Sucrose | 0.0 | 1.3 |

Table 7 illustrates the mortality of adult house flies exposed to treatments and assessed after 4 and 6 days. Sodium EDTA formulations with food additives were significantly more efficacious than sodium EDTA formulations without food additives against adult house flies, indicating that formulations are most effective as ingested toxins (Table 7). The formulation containing food additives and Silwet L77, a silicone glycol co-polymer surfactant, resulted in slower mortality than the formulation without Silwet L77.

EXAMPLE 8

Formulations were applied to the center of glass microscope slides using an Eppendorf pipette (200 μL/rep), and they were allowed to dry overnight. Adult house flies (3 day old) were anesthetized with CO$_2$ and transferred to 250 ml clear plastic cups containing a treated microscope slide, a small amount of granulated sugar, and a water reservoir. Azamethiphos treatments consisted of two 4 cm strips (1 cm wide) placed on a glass slide for each replicate. Cups were covered with fine netting secured with rubber bands. Treatments consisted of 8 replicates of 5 insect pests each. Mortality was assessed 1, 5 and 7 days after fly introduction.

TABLE 8

| Treatment[1] | Mean % Mortality 1 Day | Mean % Mortality 5 Days | Mean % Mortality 7 Days |
|---|---|---|---|
| 1. 10% NaEDTA | 2.5 | 72.5 | 87.5 |
| 2. FeEDTA (0.66% iron + 5% Na$_4$EDTA) | 30.0 | 100.0 | 100.0 |
| 3. Ferrous gluconate (0.66% iron) + 5% Na$_4$EDTA | 27.5 | 100.0 | 100.0 |
| 4. Iron saccharate (iron sugar) (0.66% iron) | 7.5 | 55.0 | 42.5 |
| 5. Ferric sulfate (0.66% iron) | 2.5 | 2.5 | 5.0 |
| 6. Ferrous sulfate (0.66% iron) | 0.0 | 5.0 | 5.0 |
| 7. Ferric chloride (0.66% iron) | 0.0 | 15.0 | 15.0 |
| 8. 25% sucrose | 0.0 | 0.0 | 0.0 |

[1]All formulations contained sucrose.

Table 8 illustrates the mortality of adult house flies exposed to treatments and assessed after 1, 5 and 7 days. High adult house fly mortalities were observed with sodium EDTA, iron EDTA and ferrous gluconate+sodium EDTA (Table 8). Some activity was also observed with iron saccharate (iron sugar). Poor activity was observed with simple iron salts (ferric sulfate, ferrous sulfate, ferric chloride), indicating the unique activity of chelated iron.

EXAMPLE 9

Formulations were applied to the center of glass microscope slides using an Eppendorf pipette (200 μL/rep) and allowed to dry overnight. Adult house flies (6 day old) were anesthetized with CO$_2$ and transferred to 4.2L Rubbermaid tubs with mesh lids. Each tub contained one treated microscope slide, a petri dish containing a sugar cube and a water reservoir. Treatments consisted of 4 replicates of 20 insect pests each. Mortality was assessed 1, 4 and 6 days after fly introduction.

TABLE 9

| Treatment | Mean % Mortality 1 day | Mean % Mortality 4 days | Mean % Mortality 6 days |
|---|---|---|---|
| 1. FeEDTA (0.66% iron + 5% NaEDTA) | 55.0 | 71.3 | 90.0 |
| 2. Ferric chloride (0.66% iron) | 3.8 | 13.8 | 16.3 |
| 3. NaEDTA (5% NaEDTA) | 8.8 | 53.8 | 70.0 |
| 4. 25% Sucrose | 0.0 | 1.3 | 1.3 |

[1]All formulations contained sucrose.

Table 9 illustrates the mortality of adult house flies exposed to treatments and assessed after 1, 4 and 6 days. High mortalities were observed with sodium EDTA and iron EDTA against adult house flies (Table 9). Poor activity was observed with ferric chloride, a simple iron salt.

EXAMPLE 10

Formulations were applied to the center of glass microscope slides using an Eppendorf pipette (200 μL/rep) and allowed to dry overnight. Adult house flies (4-5 day old) were anesthetized with CO$_2$ and transferred to 250 ml clear plastic cups containing a treated microscope slide, a small amount of granulated sugar and a water reservoir. Azamethiphos treatments consisted of two 4 cm strips (1 cm wide) placed on a glass slide for each replicate. Cups were covered with fine netting secured with rubber bands. Treatments consisted of 8 replicates of 5 insect pests each. Mortality was assessed 1, 4 and 5 days after fly introduction.

TABLE 10

| Treatment | Mean % Mortality 1 Day | Mean % Mortality 4 Day | Mean % Mortality 5 Day |
|---|---|---|---|
| 1. FeEDTA (0.66% iron + 5% Na$_4$EDTA) | 70.0 | 100.0 | 100.0 |
| 2. FeHEDP (0.24% iron + 5% NaHEDP) | 5.0 | 52.5 | 87.5 |
| 3. 10% Na$_4$EDTA | 5.0 | 80.0 | 92.5 |
| 4. 5% Na$_4$EDTA | 5.0 | 70.0 | 82.5 |
| 5. 10% NaHEDP | 5.0 | 80.0 | 90.0 |
| 6. 5% NaHEDP | 10.0 | 80.0 | 97.5 |
| 7. CuHEDP (0.8% copper + 5% NaHEDP) | 2.5 | 50.0 | 52.5 |
| 8. CuEDTA (0.8% copper + 5% NaEDTA) | 0.0 | 37.5 | 45.0 |
| 9. 25% sucrose | 0.0 | 0.0 | 0.0 |

[1]All formulations contained sucrose.

Table 10 illustrates the mortality of adult house flies exposed to treatments and assessed after 1, 4 and 5 days. High mortalities were observed with sodium HEDP, sodium EDTA, iron HEDP and iron EDTA against adult house flies (Table 10). Some activity was also observed with copper chelates of EDTA and HEDP.

EXAMPLE 11

Formulations were applied to the center of glass microscope slides using an Eppendorf pipette (200 μL/rep) and allowed to dry overnight. Adult house flies (3-5 day old) were anesthetized with $CO_2$ and transferred to 250 ml clear plastic cups containing a treated microscope slide, a small amount of granulated sugar and a water reservoir. Azamethiphos treatments consisted of two 4 cm strips (1 cm wide) placed on a glass slide for each replicate. Cups were covered with fine netting secured with rubber bands. Treatments consisted of 8 replicates of 5 insect pests each. Mortality was assessed 1, 5 and 7 days after fly introduction.

TABLE 11

| Treatment[1] | Mean % Mortality 1 Day | Mean % Mortality 5 Days | Mean % Mortality 7 Days |
|---|---|---|---|
| 1. 10% NaEDTA | 5.0 | 87.5 | 92.5 |
| 2. FeEDTA (5% NaEDTA + 0.66% iron) | 82.5 | 97.5 | 97.5 |
| 3. FeEDDS (5% NaEDDS + 0.74% iron) | 55.0 | 62.5 | 70.0 |
| 4. 25% sucrose | 0.0 | 0.0 | 2.5 |

[1]All formulations contained sucrose.

Table 11 illustrates the mortality of adult house flies exposed to treatments and assessed after 1, 5 and 7 days (I07-046). High mortalities were observed with sodium EDTA and iron EDTA against adult house flies (Table 11). Some activity was also observed with iron EDDS.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

I claim:

1. A method for killing insect pests, comprising:
   providing a pesticidal composition having a first component selected from the group consisting of a phosphonic acid chelating agent, a metal complex of the phosphonic acid chelating agent, a phosphonic acid chelating agent combined with a metal salt, and mixtures thereof, and a second component that comprises a dry food source effective as a bait edible to insect pests; and
   applying the pesticidal composition as a solid, dry form to an area infested with insect pests, such that the insect pests can ingest the pesticidal composition.

2. The method of claim 1, wherein the first component is present at an amount that is effective to kill the insect pests upon ingestion.

3. The method of claim 1, wherein the first component is present in the composition at a concentration in the range of about 0.25% to 40%.

4. The method of claim 1, wherein the first component is present in the composition at a concentration in the range of about 0.5% to 30%.

5. The method of claim 1, wherein the phosphonic acid chelating agent is selected from the group consisting of phosphonic acid, its salts, and combinations thereof.

6. The method of claim 5, wherein the phosphonic acid salt comprises a salt selected from the group consisting of a sodium salt, a potassium salt, a calcium salt, a zinc salt, an ammonium salt, an amine salt, an amide salt, and combinations thereof.

7. The method of claim 1, wherein the phosphonic acid chelating agent is selected from the group consisting of hydroxyethyl-diphosphonic acid (HEDP), aminotri(methylenephosphonic acid) (ATMP), salts of HEDP, salts of ATMP, and combinations thereof.

8. The method of claim 1, wherein the metal complex of the phosphonic acid chelating agent comprises a metal selected from the group consisting of Group IIa elements, transition metals, and combinations thereof.

9. The method of claim 1, wherein the metal complex of the phosphonic acid chelating agent comprises a metal selected from the group consisting of aluminum, copper, iron, manganese, nickel, zinc, ferric, iron, ferrous iron, and combinations thereof.

10. The method of claim 1, wherein the metal complex of the phosphonic acid chelating agent further comprises metal ions in the form of a metal salt.

11. The method of claim 10, wherein the metal salt comprises a salt selected from the group consisting of a chloride salt, an iron salt, a sulfate salt, a nitrate salt, a citrate salt, a phosphate salt, a carbonate salt, an acetate salt, a hydroxide salt, a chelate salt, a sulfide salt, a sulfite salt, a succinate salt, a gluconate salt, a lactate salt, a formate salt, a nitrite salt, a salicylate salt, a carboxylic acid salt, and combinations thereof.

12. The method of claim 1, wherein the carrier material is selected from the group consisting of wheat flour, wheat cereal, bran, molasses, vinegar, agar, gelatin, petfood, wheat, soy products, oats, corn, corn cob, vegetable oils, citrus mash, rice, fruits, fish by-products, sugars, coated vegetable seeds, coated cereal seeds, dairy products, whey powder, casein, albumen, blood meal, bone meal, yeast, fats, beer products, and combinations thereof.

13. The method of claim 1, wherein the carrier material further comprises at least one additive selected from the group consisting of attractants, phagostimulants, cellulose complexes, sand, clay, silica, polyacrylic acid polymers, polyacrylimide acid polymers, diatomaceous earth, alginate, wax, and combinations thereof.

14. A method for killing insect pests, comprising:
   providing an insecticidal composition having a first component that comprises a chelating agent formed from a phosphonic acid, the chelating agent being the only insecticidal component present, and a second component that comprises an ingestible carrier material; and
   applying the insecticidal composition to an area infested with insect pests, such that the insect pests can ingest the insecticidal composition,
   wherein the first component is present at an amount that is effective to kill the insect pests upon ingestion, and the carrier material is selected from the group consisting of water, sugars, alcohols, vinegar, plant-derived oils, mineral oils, glycerol, glycols, wheat flour, wheat cereal, bran, molasses, agar, gelatin, pet food, wheat, soy products, oats, corn, corn cob, vegetable oils, citrus mash, rice, fruits, fish by-products, coated vegetable seeds, coated cereal seeds, dairy products, whey powder, casein, albumen, blood meal, bone meal, yeast, fats, beer products, attractants, phagostimulants, cellulose complexes, sand, clay, silica, polyacrylic acid polymers, polyacrylimide acid polymers, diatomaceous earth, alginate, wax, and combinations thereof.

15. The method of claim 14, wherein the first component is present in the composition at a concentration in the range of about 0.25% to 40%.

16. The method of claim 14, wherein the first component is present in the composition at a concentration in the range of about 0.5% to 30%.

17. The method of claim 14, wherein the insecticidal composition further comprises a pH-adjusting agent.

18. The method of claim 17, wherein the pH-adjusting agent is selected from the group consisting of calcium carbonate, potassium carbonate, hydrochloric acid, potassium hydroxide, ascorbic acid, tartic acid, citric acid, and combinations thereof.

19. The method of claim 17, wherein the pH-adjusting agent is present in the composition at a concentration in the range of about 0.05 to 5.0% by weight.

20. The method of claim 14, wherein the chelating agent is selected from the group consisting of hydroxyethyl-diphosphonic acid (HEDP), aminotri(methylenephosphonic acid) (ATMP), salts of HEDP, salts of ATMP, and combinations thereof.

21. The method of claim 14, wherein the chelating agent is complexed with a transition metal to form a metal chelate.

22. The method of claim 21, wherein the metal complex of the chelating agent comprises the chelating agent combined metal ions in the form of a metal salt.

23. The method of claim 21, wherein the metal chelate comprises a metal selected from the group consisting of iron, aluminium, copper, manganese, nickel, zinc, and combinations thereof.

24. The method of claim 14, wherein the composition is effective to kill pests selected from the group consisting of aphids, leafhoppers, whitefly, sawfly larvae, caterpillars, beetles, cockroaches, earwigs, ants, flies, mosquitoes, wasps, silverfish, and combinations thereof.

* * * * *